United States Patent
Chen

Patent Number: 5,939,578
Date of Patent: Aug. 17, 1999

[54] VASOMOLOL: AN ULTRA SHORT-ACTING AND VASODILATORY VANILLOID TYPE $\beta_1$-ADRENOCEPTOR ANTAGONIST

[75] Inventor: Ing-Jun Chen, Kaohsiung, Taiwan

[73] Assignee: Tong-Ho Lin, Taipei, Taiwan; in part interest

[21] Appl. No.: 08/667,648

[22] Filed: Jun. 21, 1996

[51] Int. Cl.[6] .................................................. C07C 213/04
[52] U.S. Cl. ............................................. 560/42; 502/451
[58] Field of Search ................................ 560/42; 502/451

[56] References Cited

U.S. PATENT DOCUMENTS 3,961,071  6/1976  Koppe ...................................... 424/319

OTHER PUBLICATIONS

March, Advanced Organic Chemistry, p. 1196, 1992.

*Primary Examiner*—Robert Gerstl
*Attorney, Agent, or Firm*—Jacobson, Price, Holman & Stern, PLLC

[57] ABSTRACT

This invention is related to novel vasomolol, compounds of this invention have the following formula wherein $R_1$ represents $C_{1-4}$ alkyl group.

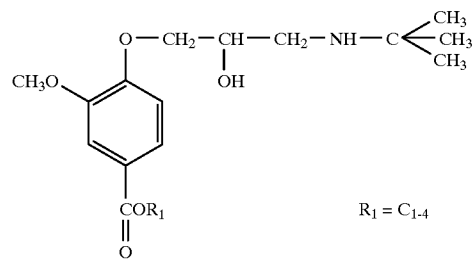

vasomolol is an ultra short-acting and vasodilatory selective $\beta_1$-adrenoceptor antagonist, and is devoid of ISA.

Vasomolol is an utra short acting and vasodilatory selective $\beta_1$-adrenoceptor antagonist, and is devoid of IA. The ultra short-acting and vsodilatory $\beta_1$-adrenoceptor blocking activities of vasomolol-a guaiacoxypropanolamine derivative of vanillic acid ethyl ester—were studied. Vasomolol (0.5, 1.0, 3.0 mg/kg, I.v.) produced a dose-dependent bradycardia rsponse, and particularly a hypotensive action with an ultra short-acting property in pentobarbital-anesthetized normotensive rats. Vasomolol's steady-state of $\beta$-blockade was attained within 10 min after initiation of an infuson and a rapid recovery from blockade took place after termination of the infusion. In isolated rat aorta, vasomolol ($10^{-6}$ M–$10^{-5}$ M) inhibit both henylephrine ($10^{-6}$ M) and High $K^+$ (75 mM)—induced smooth muscle contractions, concentration-dependently. This inhibitory effect of vasomolol was more sensitive on $K^+$ than on phenylephrine-induced contractions.

10 Claims, 13 Drawing Sheets

VASOMOLOL: AN ULTRA SHORT-ACTING AND VASODILATORY VANILLOID TYPE $\beta_1$-ADRENOCEPTOR ANTAGONIST

BACKGROUND OF THE INVENTION

β-Adrenoceptor blockers are widely used in the treatment of cardiovascular disease, including hypertension, angina pectoris, supraventricular arrhythmias, hypertrophic cardiomyopathy, and myocardial infarction. All these β-adrenoceptor blockers share the common feature of being competitive antagonists of β-adrenoceptor. They differ, however, in additional pharmacological properties, such as in the $\beta_1$-/$\beta_2$-selectivity, in the presence or absence of intrinsic sympathomimetic activity(ISA), in the membrane stabilizing activity, in the lipid versus water solubility is reported in Mount Sinai Journal of Medicine 52(7), 553, 1985(by Squire, A. et al.) and in the pharmacokinetic properties is reported in Arzneim-Forch/Drug Res. 36(1), 200, 1986 (by Harting, J. et al.). β-adrenoceptor blockers with vasodilatory effects are also important for their calcium channel blocking properties as reported in Gen. Pharmacol. 24. 1425, 1993 (by inventor group).

The ultra short-acting β-blocker(USABB) was described to be much safer than longer-acting antagonists in critically ill patients who require a β-adrenoceptor antagonist is reported in Med. Chem. 25, 1402, 1982 (by Erhardt, P. W. et al.). This benefit is attributable to the fact that continuous infusion of USABB may achieve its steady-state concentrations quickly, and that the therapeutic actions terminate rapidly when the infusion is discontinued is reported in J. Pharm. Exp. Ther. 237, 912, 1986 (by Quon, C. Y. et al.). Esmolol (formula I), a $\beta_1$-selective adrenoceptor blocker rapidly metabolized by blood and liver esterase, was thus suggested for use as a USABB in controlling supraventricular arrhythmias, preoperative hypertension, and myocardial ischemia in acutely ill patients is reported in Drugs 33, 392, 1987 (by Benfield, P. et al.). USABB with vasodilatory properties was also of interest and seems to be of much greater significance than can be accounted for simply by β-blockade alone is reported in Clin. Pharmacol. Ther. 38, 579, 1985 (by Reilly, C. S. et al.). Esterification of inactive metoprolol metabolite has shown various reduced and shorter duration systemic and β-adrenergic blocking activities than metoprolol is reported by Bodor et al. 1988). Other esmolol-type, morpholino-type, and urea-type β-blockers with USABB activities have also been reported recently in Chem. Pharm. Bull. 40, 1462, 1992 (by lguchi, S. H. et al.).

β-Adrenoceptor blockers derived from vanilloid type compounds have been partly described in previous reports (by inventor group, 1993). Vanilloid type β-blockers are a family of guaiacoxypropanolamines, chemically with 3-methoxy, 4-hydroxy benzyl nucleus that are found in pungent principles. Those vanilloid type compounds may cause the activation of sensory and autonomic cardiovascular system in vivo, but alkylation of its 4-hydroxy benzyl nucleus are devoid of pungent activity and maintain vasodilatory effect, there reported in Eur. J. Med. Chem. 27, 187, 1992 and 37, 938, 1994 (by inventor group). To date, very few β-blockers with vanilloid base was described for its USABB activity (Iguchi, S. H. et al, 1992). The present study was further aimed at investigating the pharmacological properties of vasomolol, a derivative of vanillic acid or its ethyl ester with a vanilloid base, for its possible ability to bind to β-adrenoceptors, its relative selectivity for β-adrenoceptors, intrinsic sympathomimetic activity, and particularly its USABB and vasodilatory activities

DETAILED DESCRIPTION

SUMMARY OF THE INVENTION

An object of the present invention is to provide new vasomolol derivatives of formula II, their pharmaceutically acceptable salt and compositions comprising the same which are ultra short acting, vasodilatory selective $\beta_1$-drenoceptor antagonist, and is devoid of ISA in wherein $R_1$ represents hydrogen, $C_{1-4}$ alkyl group.

Another object of the present invention is to provide vasodilatory selective $\beta_1$-adrenoceptor antagonist compositions and a method of treatment of patients in need of treatment.

Another object of the present invention is to provide process for the preparation of the novel compounds and to pharmaceutically compositions comprising the same.

I. Preparation Methods

Figure 1:
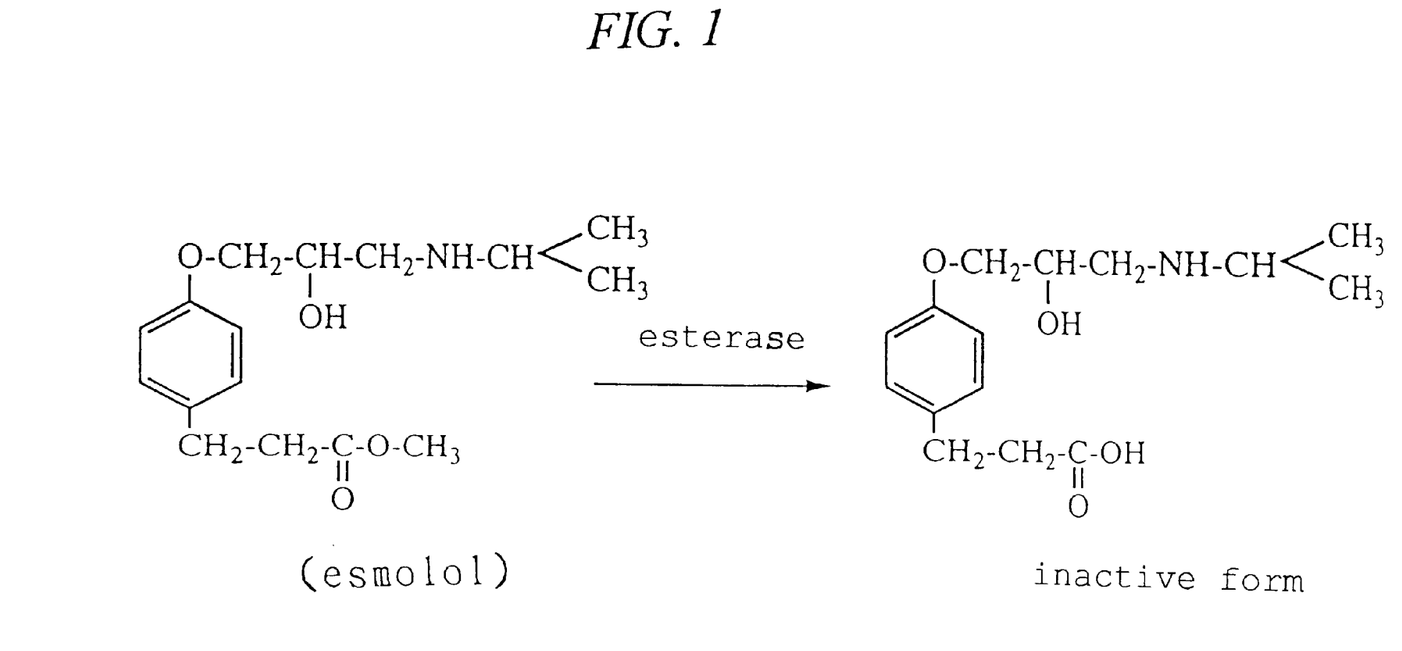
FIG. 1.
Esmolol was metabolized by blood and liver esterase
Figure 2:
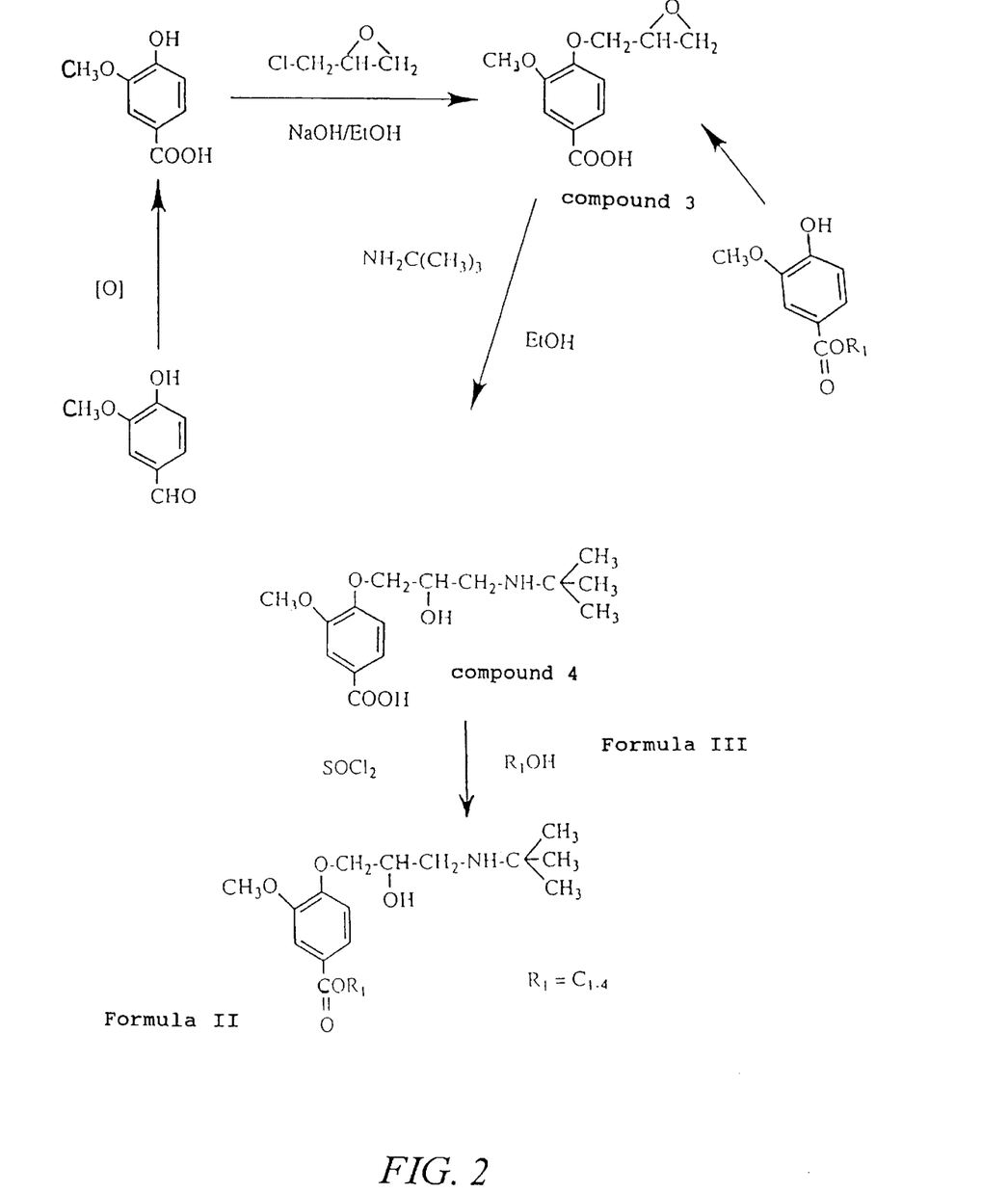
FIG. 2.
Chemical structure of vasomolol

The preparation methods of formula II are shown in FIG. 2. The synthetic reactions are preferably carried out in the alkaline solution of starting materials, like vanillin, vanilliic acid and its ester compounds.

According to the reaction scheme herein below (FIG. 2) vanilliic acid was synthesized from vanillin, then treated with epichlorohydrine gave compound 3. Amination compound 3 with butylamine in alcoholic solution produced the compound 4; esterized compound 4 with compound of formula III give compound of formula II.

According to the reaction other scheme herein below (FIG. 2) compound of formula IV was synthesized from vanillin, or vanillic acid with compound of formula III separately, then treated with epichlorohydrine gave compound of formula V. Amination compound of formula V with butylamine in alcoholic solution produced the compound of formula II. on responds the process, the epichlorohydrine may be replaceable with epibromohydrine give the result for same alike produced.

In the compound of formula II, III, IV and V in wherein $R_1$ represents hydrogen, $C_{1-4}$ alkyl group. These structures of all compounds described above were assigned according to the IR, $^1$H—NMR, $^{13}$C—NMR, MS, elemental analytical data.

The vasomolol derivatives of formula II according to the present invention and also their salts display useful pharmacological properties, Suitable salts of compounds of the formula II are the sodium salts, calcium salts, potassium salts, or magnesium salts etc. pharmaceutically acceptable salts.

The formula II derivatives and pharmaceutically acceptable salt are ultra short acting, vasodilatory selective $\beta_1$-adrenoceptor antagonist, and is devoid of ISA. Those compounds are useful as a medicine for the prevention arrhythmia. The following tests are given for the pharmacological activity.

II. Phamacological Activity

Measurement of blood pressure and heart rate

The method reported in Gen. Pharmacol. 24, 1425, 1993 (by inventor group), drug vasomolol (0.5, 1.0, 3.0 mg/kg)

esmolol (300 μg/kg/min)

phenylephrine (10 μg/klg, i.v.)

Results

Intravenous injection of vasomolol(0.5, 1.0, 3.0 mg/kg) produced a hypotensive action and a decrease in heart rate in pentobarbital-anesthetized Wistar rats (Table 1). Administrating esmolol in the same doses also showed similar to those of vasomolol. The bradycardia duration of both vasomolol and esmolol were a little less than 10 min. In the contrast, propranolol produced a longer bradicardia effect which persisted for more than 60 min. Intravenous infusion of vasomolol and esmolol (300 μg/kg/min) could not significantly inhibit phenylephrine 10 μg /klg, i.v.)—induced pressor response in reserpinized rats (data not shown).

Effects of vasomolol on β-blockade and duration of action method

Vasomolol (100 μg/kg/min) was infused consecutively into a femoral vein in pentobarbital-anesthetized rats. Each perfusion was maintained for 60 min. Before and during the infusion of vasomolol and esmolol, at 10-min intervals, bolus i.v. injections of (-) isoproterenol (0.5. μg/kg) were administered to assess the level of β-blockade. (-) lsoproterenol injections were also continued for 60 min. after termination of the highest dose of vasomolol and esmolol to assess the duration of β-blockade reported in J. Pharm. Exp. Ther. 237, 912, 1986 (by Quon, C. Y. et al.). The percentage of inhibition of the (-)isoproterenol-induced tachycardia parameter of β-blockade—was calculated during and after infusions of vasomolol.

drug
isoproterenol (0.5 μg/kg)
vasomolol (0.5, 1.0, 3.0 mg/kg)
esmolol (300 μg/kg/min)

Results

Repeated isoproterenol administrations in rats at 10 min intervals produced increases in heart rate that were reproducible in magnitude for a 30 min. period. The time courses of β-adrenergic receptor blockade during infusions of vasomolol and esmolol are shown in FIG. 2. The onset of β-blockade was rapid and steady-state level of blockade occurred within 10 min. after initiating each infusion rate and remained constant through each infusion period. β-blockade caused by vasomolol and esmolol disappeared rapidly after the termination of infusion. The time required for 50% recovery averaged 9.5±1.0 min.(mean±S.E.M.).

Effects of vasomolol on pheylephrine and high $K^+$ induced contractions of isolated rat aorta Measurement of vasodilatation effect method Male rats weighing 200–250 g were sacrificed by a blow on the head and the thoracic aorta was removed and cleaned of all loosely adhering tissue. The thoracic aorta was cut from an area close to the aortic arch, immediately placed in a physiological solution, and trimmed to 2–4 mm in length as described in Gen. Pharmacol. 24, 1425, 1993 (by inventor group) The rings were then mounted with a tension of 1.0 g between parallel hooks in a 10 ml organ bath containing a physiological solution(mM):NaCl 112; KCl5.0; $NaHCO_3$ 25; $KH_2PO_4$1.0; $CaCl_2$ 1.25; $MgSO_4$ 1.2; and glucose 11.5]. The bath was maintained at 37° C. and aerated with a mixture of 95% $O_2$ and 5% $CO_2$. The tension of the aortic rings were recorded isometrically by means of a force displacement transducer (UGO, Model 7004, Italy) connected to an amplifier (COULBOURN, Model S72-25, U.S.A.). Before the start of the experiments, all preparations were allowed to equilibrate for 1.0 hr in the physiologic solution.

Measurement of atrial rate and tension

Guinea-pigs (Hartley) of either sex weighing between 350 and 500 g were sacrificed by a blow on the head. Their hearts and trachea were quickly excised and excess tissue was removed. Spontaneously-beating right atria were removed from the hearts and mounted in a 10 ml organ bath with one end fixed and the other end connected to a force displacement transducer (Grass, Model 13-6615-50, U.S.A). The frequency of contraction was measured on a separate channel by a tachometer (GOULD WindoGraf, Model 40-8474-20, U.S.A). The experiments were carried out at 32.5° C. in a Krebs solution of the following composition (mM) : NaCl 113, KCl 4.8, $CaCl_2$ 2.2, $KH_2PO_4$ 1.2, $MgCl_2$ 1.2, $NaHCO_3$ 25, Dextrose 11.0; bubbled with a 95% $O_2$–5% $CO_2$ mixture. The atrial strip was prestretched to a baseline tension of 0.2 g. The atria were equilibrated for 90 min in an aerated (95% $O_2$–5% $CO_2$) Krebs solution before the experimental protocols were initiated, For the assessment of β-adrenergic blocking activity, a control cumulative concentration-response curve to the chronotropic effect of (-) isoproterenol was established. The atria were then allowed a 30–60 min washout period to estabilize, after which time various concentrations of the test compound were incubated with the atrium 30 min before the cumulative concentrations of the (-) isoproterenol ($3\times10^{10}$–$10^5$ M) was added. All responses to (-) isoproterenol were calculated as a percentage of the maximum control response to (-) isoproterenol.

In the isolated left atria, quiescent left atria were dissected free of connective tissue and mounted in organ chambers under a resting tension of 0.5 g. Atria were bathed in an aerated Kreb's solution(32.5° C.) and were driven at 2-s intervals via two platinum electrodes placed at either side of the atrium. β-Adrenoceptor antagonist activity was determined as follows. Cumulative concentration-response curves to the positive inotropic effects of (-) isoproterenol were obtained in the absence and presence of various concentrations of a test compound. An incubation time of 30 min was allowed for the test compound. Data were calculated as a percentage of the increase in force induced by (-) isoproterenol.

Results

Figure 3:
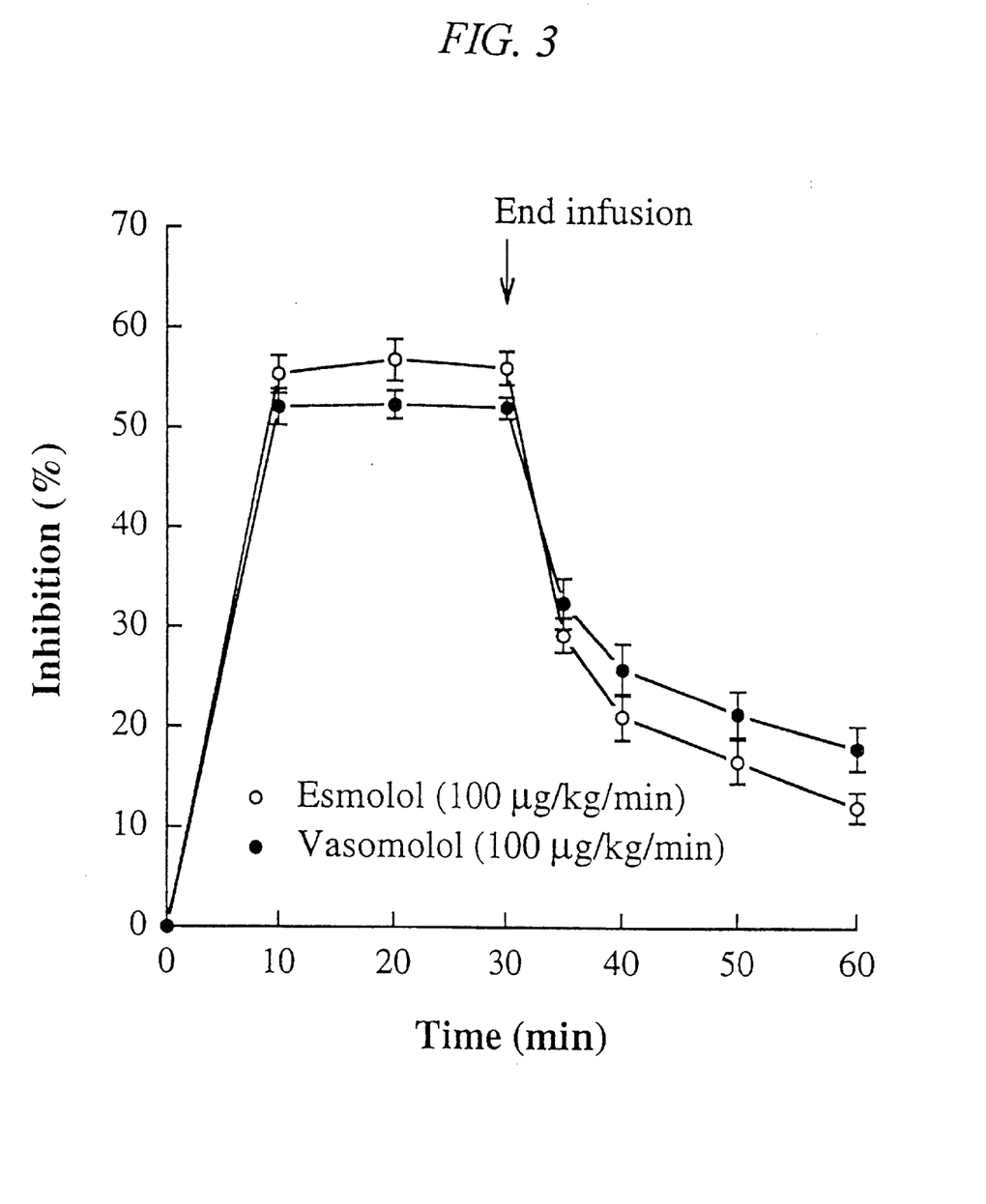
FIG. 3.
Percentage of inhibition of isoproterenol-induced tachycardia during a 30 min infusion of vasomolol and recovery from beta blockade after termination of vasomolol infusion (n=6)

In the isolated rat thoracic aorta, contractions induced by phenylephrine ($10^5$ M) and high $K^+$ (75 mM) were significantly inhibited by the adding with vasomolol ($10^6$–$10^5$ M) in the isolated rat aorta. The relaxation profit of vasomolol was more sensitive in high $K^+$ than in phenylephrine-contracted aorta preparations (FIG. 3).

Effects of vasomolol on β-adrenoceptor activity in guinea-pig atria and trachea

Contractility of isolated tracheal strips method

Guinea-pig trachea were cleaned of extraneous connective tissue and cut into spiral strips as described in Gen. Pharmacol. 24, 1425, 1993 (by inventor group). This spiral strip was cut into two equal segments and both were suspended in organ baths filled with 20 ml of Kreb's solution. Temperature was maintained at 32.5° C. and the solution was gassed with 95% $O_2$–5% $CO_2$. An initial basal tension of 2 g was applied to each tracheal strip and the tissue was allowed to gain tone spontaneously until a steady level was reached (60 min). The tracheal preparations were pretreated with phenoxybenzamine (50 μM for 30 min followed by thorough wash-out as described in Br. J. Pharmacol. 57, 369, 1976 (by O'Donnell, S. R. et al.) to prevent extraneuronal uptake and to block α-drenoceptors. For the determination of β-adrenoceptor antagonist activity, cumulative concentration-response curves to the relaxant effects of isoproterenol were obtained in the absence and presence of a test compound (60 min incubation time). Data were calculated as a percentage of the maximum relaxation induced by (-) isoproterenol.

drug
Vasomolol ($5\times10^{-8}$–$10^{-6}$ M)
isoproterenol
propranolol

Results

Figure 4:
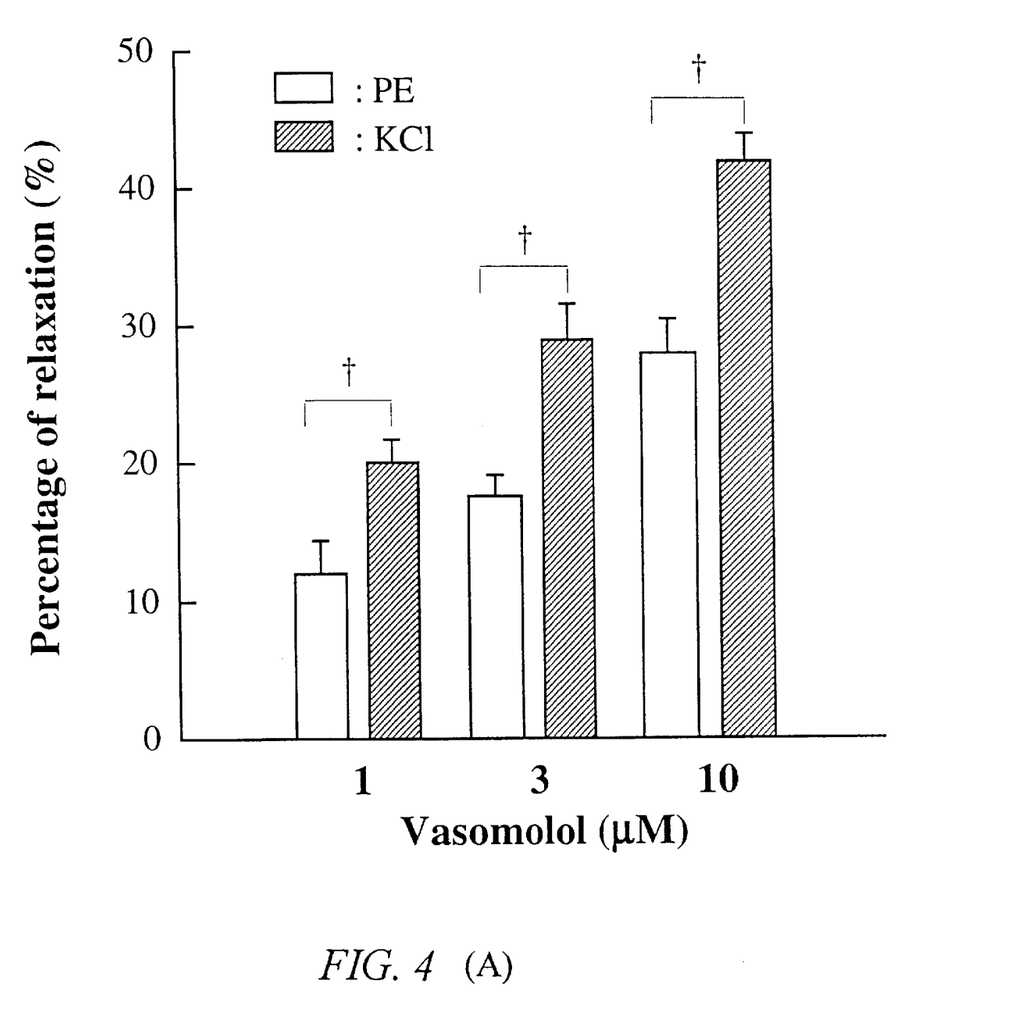
FIG. 4.
Effects of vasomolol on (A) phenylephrine($10^{-5}$ M) and (B) high K$^+$(75 mM) induced contraction in rat thoracic aorta.
Each value represents the mean±SEM of six determinations.

Vasomolol antagonized isoproterenol-induced positive chronotropic actions in isolated guinea-pig right atrial strips. Vasomolol ($5 \times 10^{-8}$–$10^{-6}$ M) caused a dose-dependent parallel shift to the right of the isoproterenol concentration-response curves. The results of a typical experiment with right atria is illustrated in FIG. 4A. In electrically driven guinea-pig left atrial strips, vasomolol also antagonized isoproterenol-induced positive inotropic responses and produced dose-dependent rightward shifts of the cumulative concentration-response curves to isoproterenol. Potential time-dependent changes in agonist potency were monitored by control experiments in which both the first and second isoproterenol concentration-response curves were carried out without antagonist. There was a decrease in the potency of isoproterenol in the second concentration-response curve that was statistically significant (data not shown). The CR for antagonists was corrected for this change in sensitivity. Vasomolol was more potent than atenolol, slightly more potent than metoprolol, and was less potent than propranolol in β-adrenoceptor blocking activity. The $pA_2$ values and slopes of regression lines are indicated in Table 2. Vasomolol ($5 \times 10^8$–$10^6$ M) also competitively antagonized (−) isoproterenol-induced relaxation from the spontaneous tone of reserpinized guinea-pig tracheal strips and thus produced parallel shifts to the right of the agonist concentration-response curves (FIG. 4B). The CR for antagonists was adjusted for the same reason that it was for left atrial strips. Vasomolol was less potent than propranolol in $β_2$-adrenoceptor blocking action. The $pA_2$ values and slopes of regression lines are indicated in Table 2.

$β_1$:$β_2$-selectivity of vasomolol.

Propranolol Intrinsic sympathomimetic activity method

Animals were pretreated with reserpine (10 mg/kg, i.p.) 24 hr prior to the experiment described in Naunyn-Schmiedeberg's Arch. Pharmacol. 311, 237, 1980 (by Kaumann, A. J. et al.). All preparations including isolated right atria and left atria strips were studied. The concentration-response curve was obtained by cumulative addition of (−) isoproterenol, propranolol, atenolol or vasomolol.

Results

The $β_1$/$β_2$-selectivity ratio was obtained from the antilogarithm of the difference between the mean $pA_2$ values obtained from the right atria and trachea as described in J. Pharm. Pharmacol. 57, 369, 1972 (by Baird, J. R. C. et al.). Vasomolol was 39.8 times more potent on right atria than on trachea, I.e. was selective for $β_1$-adrenoceptors. Propranolol was only 1.3 times more potent on right atria than on trachea and was, therefore, considered to be non-selective (Table 2).

Figure 5:
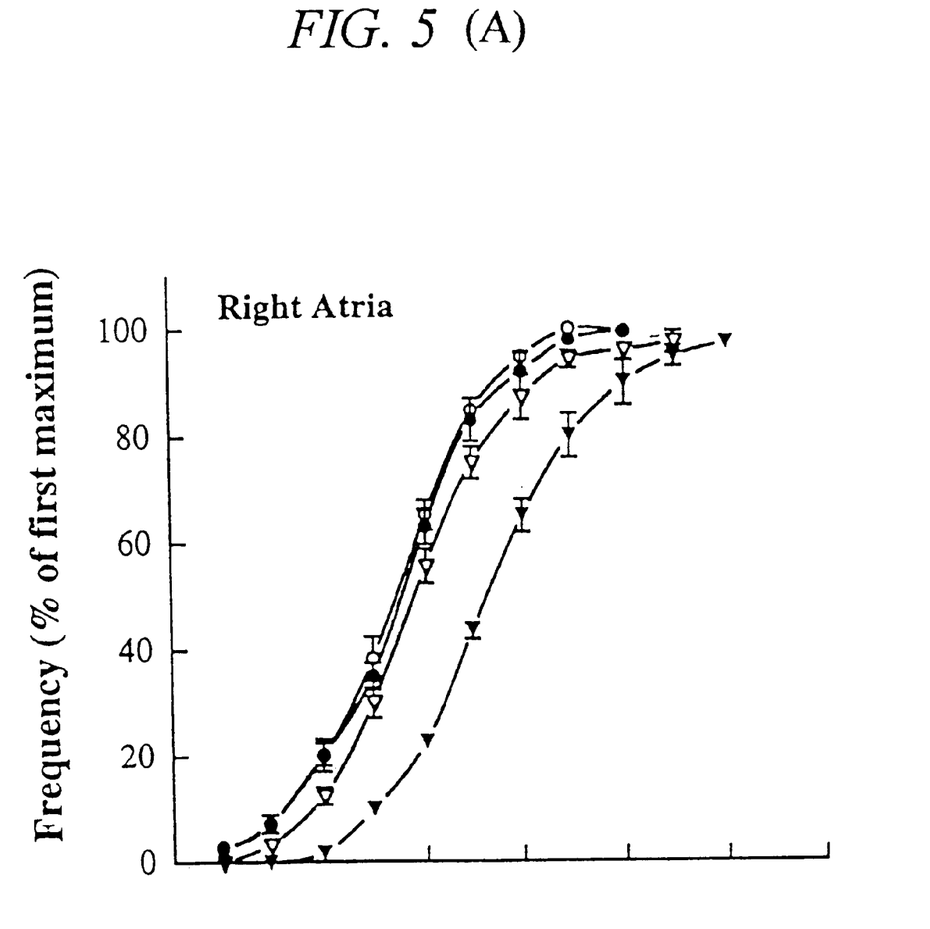
FIG. 5.
The effects of vasomolol on responses in guinea-pig atria and trachea.
Mean cumulative concentration-response curves are shown for the positive chronotropic responses to (–) isoproterenol in spontaneously-beating guinea-pig right atria, positive inotropic responses to (–) isoproterenol in electrically driven guinea-pig left atria, and relaxant effects to (–) isoproterenol in guinea-pig spontaneous tone tracheal strips in the absence (○) or presence of 0.01 (●), 0.1 (∇), 1 (▼) or 10 (◇) μM of vasomolol.
Points show mean values±SEM in from six to eight individual experiments.

Lack of intrinsic sympathomimetic activity of vasomolol drug esmolol vasomolol, atenolol, propranolol isoproterenol Results The frequency of contraction of right atria and tension developed by left atrial strips from reserpinized guinea-pigs were measured against cumulatively increasing concentrations of vasomolol, atenolol, propranolol or isoproterenol. As shown in FIG. 5, isoproterenol produced concentration-dependent increases in heart rate and contractility with a maximum increase at $10^6$ M. Vasomolol did not induce an increase in the heart rate or contractility, but caused negative inotropic and chronotropic effects in concentrations at $10^{-5}$ M or above. Propranolol also produced negative inotropic and chronotropic effects, and such depressant effects usually increased steeply with concentration, leading in most cases to arrest or unexcitability of the preparation at concentrations between $10^{-4}$ and $10^{-3}$ M.

Effects of vasomolol on radioligand binding studies.

Receptor binding experiments.

method

Pig's heart were obtained from a local slaughterhouse immediately after the animals had been killed and transported to our laboratory in ice-cold buffer (250 mM sucrose/ 50 mM Tris [hydroxymethyl] aminomethane HCl/1 mM magnesium chloride, pH 7.4). Various heart tissues were removed and prepared as detailed as described in Cardiovasc. Res. 25, 764, 1991 (by Bjornerheim, R. et al.). In the test for receptor binding, the ventricles were placed in ice-cold buffer and all subsequent procedures were carried out at 4° C. The tissue was homogenised in 20 volumes of TE buffer (10 mmole.litre$^{-1}$ Tris-HCl, 1 mmole.litre$^{-1}$ EDTA, 0.1 mmole.litre$^{-1}$ ascorbic acid, pH 7.4) with three 12-s pulses using a Polytron homogenizer (Kinematica, Model PT 3000, Switzerland). The homogenate was filtered with pressure through muslin and the filtrate centrifuged for 10 min at 1000 g to remove connective tissue, unbroken cells and cell debris. The supernatant was centrifuged again at 10,000 g for 12 min. This second supernatant was then centrifuged for 15 min at 30,000 g and the final pellet was suspended in a assay buffer (75 mM Tris HCl/25 mM $MgCl_2$, pH 7.4).

Protein was determined by the method in Anal. Biochem. 72, 248, 1976 (by Bradford, M. M. et al.). This membrane preparation has been described in Biochem. Biophys. Acta. 541, 334, 1978 (by Ciaraldi, T. et al.). The binding assay of [$^3$H]-DHA was carried out as described in Biochem. Biophys. Res. Commun. 60, 703, 1974 ( by Lefkowitz, R. J. et al.) with slight modifications. [$^3$]-DHA and ventricular membranes (200–300 μg) were incubated for 60 min at 25° C. with and without the addition of 1 μM alprenolol, in 75 mM Tris-HCI buffer comprising $MgCl_2$ 25 mM, to make a final volume of 250 μl. In competitive binding experiments, the competing agent was added directly to the incubation mixture. The incubation was terminated by addition of 1 ml of ice-cold assay buffer followed by immediate filtration through Whatman GF/C glass fiber filters supported on a 12-port filter manifold (Millipore). The filters were immediately washed three times with 5 ml of ice-cold assay buffer and dried in an oven at 60° C. for 2 hr prior to adding 5 ml of Triton-toluene based scintillation fluid.

Membrane-bound

[$^3$H]-DHA trapped in the filters was counted in a Wallac LKB 1211 rackbeta liquid scintillation counter with an efficiency of 41%. In each experiment, non-specifically bound [$^3$H]-DHA was determined by incubating membrane protein and [$^3$H]-DHA with 1 μM alprenolol. Specific binding was thus obtained by deducing this value from the total binding of [$^3$H]-DHA for each sample.

Result

Figure 6:
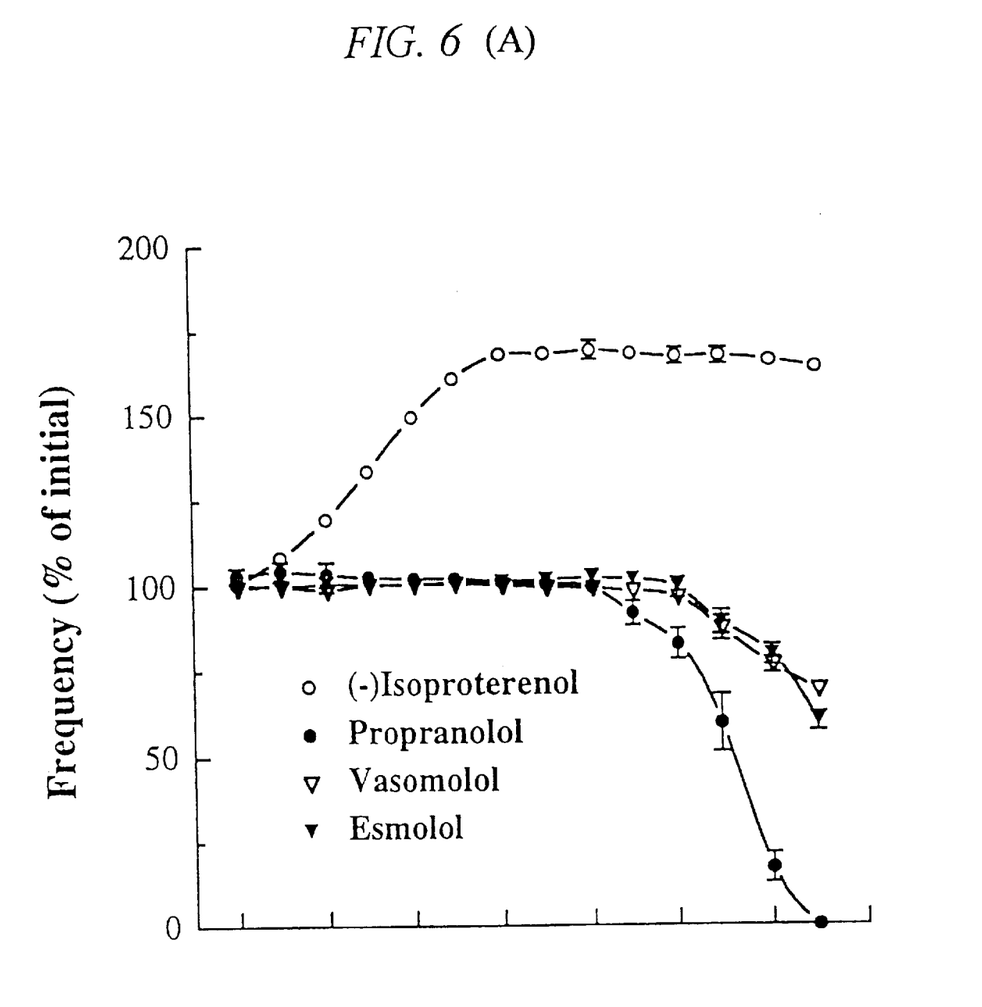
FIG. 6.
Stimulant and depressant effects of (–) isoproterenol, propranolol, vasomolol and esmolol on frequency of spontaneously-beating right atria and tension developed by left atrial strips driven at 2 sec intervals from reserpinized guinea-pigs.
Cumulative concentration-response curves were determined at 32.5° C. for four agents identified in panels (A) and (B). All measurements are expressed as mean percentages of the control frequency or force in the same preparation. Points shows mean values±SEM from four to six individual experiments.
Figure 7:
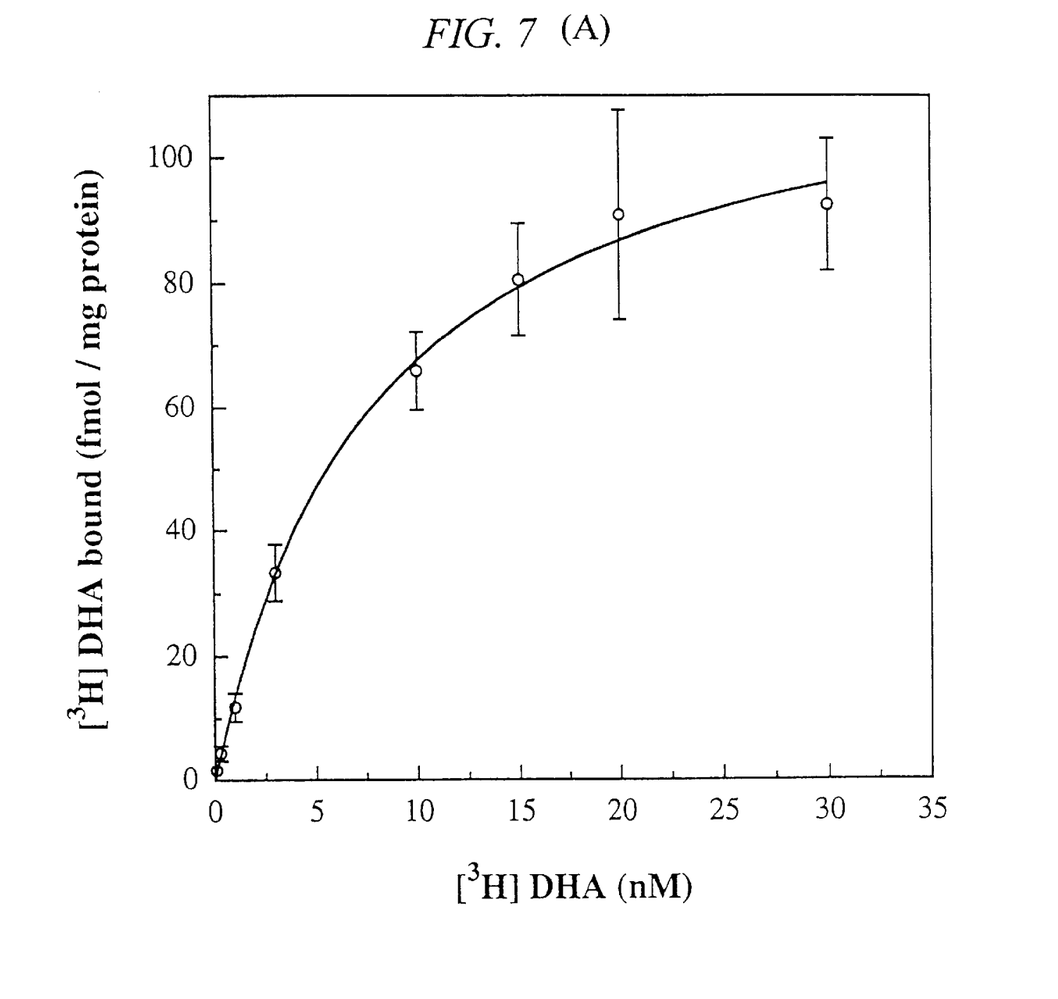
FIG. 7
[$^3$H]dihydroalprenolol([$^3$H]DHA) binding curve with pig ventricular membranes.
The membrane fractions were incubated with increasing concentrations of [$^3$H]-DHA (0.1–30 nM) in the presence (nonspecific) and absence (total) of 10 μM (–) alprenolol. The inset shows a Scatchard analysis of specific [$^3$H]-DHA binding to the membrane fraction. Each point represents the mean±SEM of three experiments, and conducted in duplicate.
Figure 8:
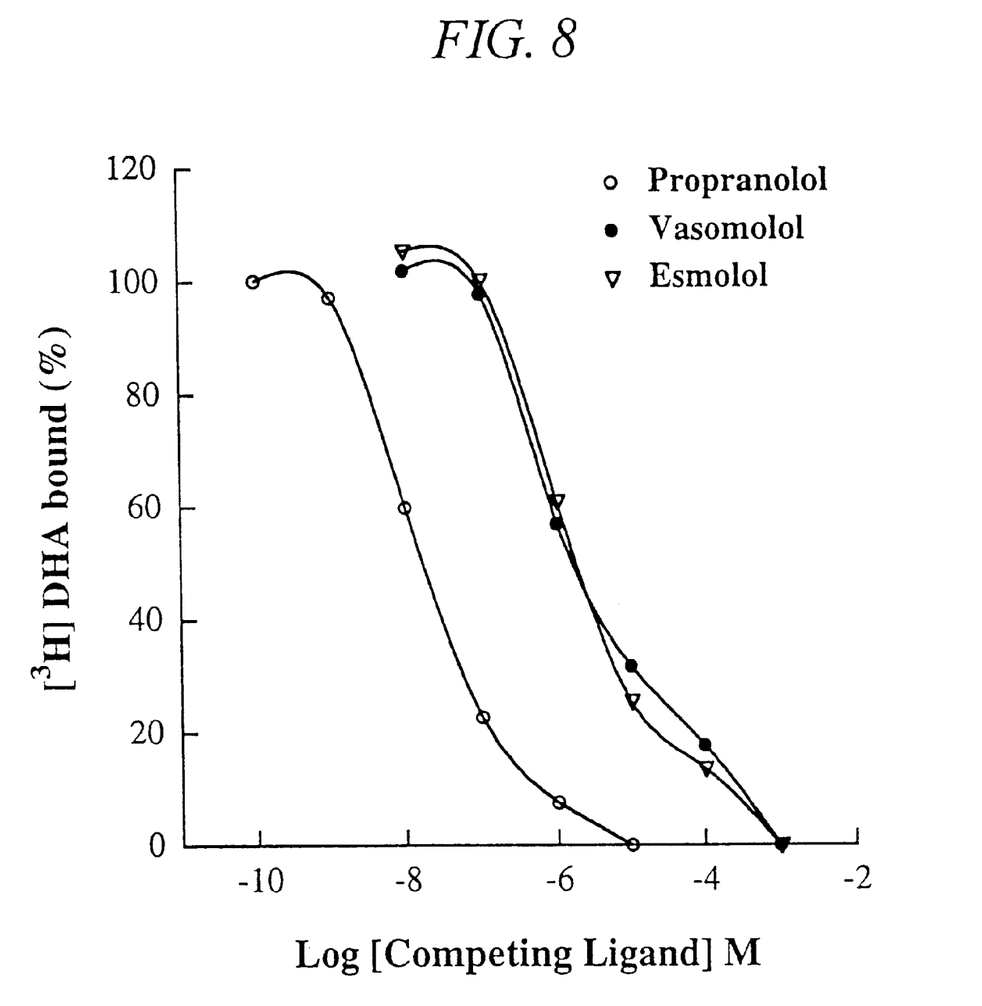
FIG. 8.
Inhibition of [$^3$H]-DHA specific binding to pig ventricular membrane β-adrenoceptors by various β-adrenoceptor blocking gents. All incubations were performed as described in the method section. Data shown are the means of three independent duplicate determinations.

[$^3$H]-DHA was bound to guinea-pig ventricular membranes in a saturable manner as illustrated in FIG. 6. The concentration dependence of [$^3$H]-DHA binding was studied with labeled compound concentrations ranging from 0.1 to 30 nM. Scatchard analysis (Ann. N. Y. Acad. Sci. 51, 660, 1949) to determine the affinity and number of binding sites is shown in the inset. The equilibrium dissociation constant (Kd) was 8.1±0.9 nM (mean±S.E.M.), and the maximum binding capacity ($B_{max}$) was 120.3±6.0 fmol/mg protein (mean±S.E.M.) at 25° C. The binding of [$^3$H]-DHA reached equilibrium in approximately 20 min and maintained it for up to 90 min (data not shown). FIG. 7 demonstrates the competition curves of β-adrenoceptor antagonists for [$^3$H]-DHA binding sites in the ventricular membranes. The $IC_{50}$ value (mean±S.E.M.) of (–) propranolol, a nonselective β-antagonist, was 33.1±4.5 nM. The $IC_{50}$ values of vasomolol and esmolol were 4.7±1.5 and 5.0±1.3 (uM), respectively. The order of potency of β-adrenoceptor inhibiting [$^3$H]-DHA binding was (–) propranolol>>vasomolol= esmolol.

EXAMPLE 1

Slowly added of 30% aqueous sodium hydroxide to 15.2 g vanillin under lower 25° C. Mixed with 5 mol times chlorohydrin, 3 mol times t-butylamine. The mixture was heated under reflux at 55° C. for 1 hr. The mixture was evaporated in a rotary evaporator. There residural product was recrystallized from dichloromethane to afford [4'-(2-hydroxy-3-(tert-butylamino)propoxy)-3'-methoxy]-benzoic acid.
mp: 108–110° C.
$^1$H—NMR(CDCl$_3$):

| | | |
|---|---|---|
| δ | 1.20 | (s, 9H, CH$_3$ x3), |
| | 2.40 | (brs, 1H, OH exchangeable), |
| | 290–3.27 | (m, 2H, CH$_2$NHC), |
| | 3.88 | (s, 3H, OCH$_3$), |
| | 4.06–4.19 | (m, 3H, ArOCH$_2$CH(OH)), |
| | 5.78 | (s, 1H, NH), |
| | 6.90–7.67 | (m, 3H, Ar), |
| | 12.54 | (br s, 1H, COOH). |

IR(KBr)
3250,1700 (cm$^{-1}$).
MS(m/z):298[M+H]$^+$

EXAMPLE 2

Slowly added of 5 times volume absolute ethanol, and equimultiple mol SOCl$_2$ was heated under reflux at 55° C. for 1 hr. The mixture was evaporated in a rotary evaporrator. There residural product was recrystallized from propanol and ether to afford [4'-(2-hydroxy-3-(tert-[4'-(2-hydroxy-3-(tert-butylamino)propoxy)-3'-methoxy]-benzoate.
mp: 160–162° C.
$^1$H—NMR(CDCl$_3$):

| | | |
|---|---|---|
| δ | 1.19 | (s, 9H, CH$_3$ x3), |
| | 1.27–1.34 | (t, 3H, COOCH$_2$CH$_3$), |
| | 2.42 | (bs, 1H, OH exchangeable), |
| | 2.72–2.96 | (m, 2H, CH$_2$NHC), |
| | 3.82 | (s, 3H, OCH$_3$), |
| | 4.06–4.20 | (m, 3H, ArOCH$_2$CH(OH)), |
| | 4.23–4.34 | (q, 2H, COOCH$_2$), |
| | 5.78 | (s, 1H, NH), |
| | 6.90–7.67 | (m, 3H, Ar), |
| | 12.54 | (brs, 1H, COOH). |

BRIEF DESCRIPTION OF THE DRAWINGS

Table 1
Blood pressure and heart rate responses to intravenous injection of vasomolol, esmolol and propranolol in pentobarbital-anesthetized normotensive rats.
Table 2
β-adrenoceptor blocking potency and $\beta_1/\beta_2$-selectivity of vasomolol and propranolol on guinea-pig in vitro preparations.

The $pA_2$ values and slope values were calculated from individual Schild plots by regression analysis. The $\beta_1/\beta_2$-selectivity ratio was obtained from the antilogarithm of the difference between the mean $pA_2$ values obtained from right atrium and trachea.

TABLE 1

Blood pressure and heart rate responses to intravenous injection of vasomolol, esmolol and propranolol in pentobarbital-anesthetized normotensive rats.

| Compd | Dose (mg/kg) | BP change (mm Hg) | HR change (bpm) | bradycardia duration (min) |
|---|---|---|---|---|
| Vasomolol | 0.5 | −4.5 ± 1.4 | −20.0 ± 2.3 | 3.5 ± 0.7 |
| | 1.0 | −6.5 ± 1.9 | −34.5 ± 2.8 | 7.2 ± 0.8 |
| | 3.0 | −10.8 ± 1.2 | −50.0 ± 3.4 | 8.0 ± 1.2 |
| Esmolol | 0.5 | −4.0 ± 0.8 | −25.7 ± 2.4 | 3.7 ± 0.6 |
| | 1.0 | −6.3 ± 1.3 | −37.5 ± 3.6 | 6.0 ± 1.3 |
| | 3.0 | −8.7 ± 0.9 | −58.2 ± 4.7 | 7.5 ± 1.1 |
| Propranolol | 0.1 | 3.9 ± 1.0 | −30.7 ± 3.8 | >60 |
| | 0.5 | 7.0 ± 1.6 | −50.6 ± 8.1 | >60 |
| | 1.0 | 9.5 ± 1.1 | −65.0 ± 8.9 | >60 |

Data were expressed as mean ± SEM (n = 8).

TABLE 2

$\beta$-adrenoceptor blocking potency and $\beta_1/\beta_2$-selectivity of vasomolol and propranolol on guinea-pig in vitro preparations. The $pA_2$ values and slope values were calculated from individual Schild plots by regression analysis. The $\beta_1/\beta_2$ -selectivity ratio was obtained from the antilogarithm of the difference between the mean $pA_2$ values obtained from right atrium and trachea.

| β blocker | β₁ pA₂ value* Right atrium (slope) | β₁ pA₂ value* Left atrium (slope) | β₂ pA₂ value* Trachea (slope) | β₁/β₂- selectivity ratio |
|---|---|---|---|---|
| Vasomolol | 7.41 ± 0.05 (0.90 ± 0.04) | 7.44 ± 0.03 (0.89 ± 0.02) | 5.81 ± 0.11 (0.81 ± 0.06) | 39.8 |
| Propranolol | 8.40 ± 0.06 (0.92 ± 0.05) | 8.46 ± 0.07 (0.87 ± 0.07) | 8.28 ± 0.09 (0.85 ± 0.08) | 1.3 |

*$pA_2$ values were obtained from the formula $pA_2$ = [log (DR-1) − log molar concentration antagonist]. Each $pA_2$ value was the mean ± SEM of six to eight experimental results.

What we claim is:

1. A process for preparing a compound, or an acid addition salt thereof, having the formula wherein $R_1$ is hydrogen or a $C_1$–$C_4$ alkyl group, said process comprising reacting vanillin with sodium hydroxide to form vanillic acid;

treating said vanillic acid with epichlorohydrin or epibromohydrin to form a compound having the formula aminating said compound having the formula with t-butylamine to form [4'-(2-hydroxy-3-(tert-butyl amino)propoxy)-3'-methoxy]-benzoic acid having the formula optionally esterifying said [4'-(2-hydroxy-3-(tert-butyl amino)propoxy)-3'-methoxy]-benzoic acid with $R_1OH$ to form said compound having the formula

2. The process as defined in claim 1
   wherein said treating step is performed in an alkaline solution.
3. The process as defined in claim 2
   wherein said alkaline solution comprises sodium hydroxide.
4. The process as defined in claim 3 wherein said alkaline solution further comprises ethanol.
5. The process as defined in claim 1
   wherein said aminating step is performed in an alcoholic solution.
6. The process as defined in claim 5
   wherein said alcoholic solution comprises ethanol.

7. The process as defined in claim 1 wherein said esterizing step further comprises esterizing [4'-(2-hydroxy-3-(tert-butyl amino) propoxy)-3'-methoxy]-benzoic acid in the presence of SOCl$_2$.

8. The process as defined in claim 1 wherein R$_1$OH is ethanol.

9. A compound made by the process defined in claim 1.

10. The process for preparing a compound, or an acid addition salt thereof, having the formula wherein R$_1$ is hydrogen or a C$_1$–C$_4$ alkyl group, said process consisting essentially of reacting vanillin with sodium hydroxide to form vanillic acid;

treating said vanillic acid with epichlorohydrin or epibromohydrin in an alkaline solution to form a compound having the formula aminating said compound having the formula with t-butylamine in an alcoholic solution to form [4'-(2-hydroxy-3-(tert-butyl amino)propoxy)-3'-methoxy]-benzoic acid having the formula optionally esterifying said [4'-(2-hydroxy-3-(tert-butyl amino)propoxy)-3'-methoxy]-benzoic acid with R$_1$OH in the presence of SOCl$_2$ to form said compound having the formula

* * * * *